United States Patent [19]

Wong

[11] Patent Number: 4,475,972
[45] Date of Patent: Oct. 9, 1984

[54] IMPLANTABLE MATERIAL

[75] Inventor: Edward W. C. Wong, Lexington, Mass.

[73] Assignee: Ontario Research Foundation, Mississauga, Canada

[21] Appl. No.: 370,661

[22] Filed: Apr. 22, 1982

Related U.S. Application Data

[63] Continuation-in-part of Ser. No. 309,692, Oct. 8, 1981, abandoned.

[30] Foreign Application Priority Data

Oct. 1, 1981 [CA] Canada .................................... 387143
Mar. 2, 1982 [GB] United Kingdom ................. 8206082

[51] Int. Cl.³ ........................ B65H 81/00; A61F 1/00
[52] U.S. Cl. ......................................... 156/167; 3/14; 156/175
[58] Field of Search ............... 156/167, 172, 175, 173, 156/169, 396, 166, 174; 264/205, 209.2, 210.8, 8, 176 F, 204; 428/398, 36, 903; 3/1.4, 1

[56] References Cited

U.S. PATENT DOCUMENTS

| | | | |
|---|---|---|---|
| 2,988,469 | 6/1961 | Watson | 264/5 |
| 3,490,975 | 1/1970 | Lightwood et al. | 156/167 |
| 3,554,851 | 1/1971 | Modigliani | 156/174 |
| 3,787,265 | 1/1974 | McGinnis et al. | 156/167 |
| 3,801,400 | 4/1974 | Vogt et al. | 156/167 |
| 4,021,281 | 5/1977 | Pall | 156/167 |
| 4,044,404 | 8/1977 | Martin | 3/1.4 |
| 4,116,738 | 9/1978 | Pall | 156/167 |
| 4,323,525 | 4/1982 | Bornat | 3/1.4 |

Primary Examiner—Michael Ball
Attorney, Agent, or Firm—Sim & McBurney

[57] ABSTRACT

Porous polymeric material, which, in tubular form, is suitable for use as a vascular graft, is made by a procedure wherein polymeric fibres are wound on a mandrel while overlying fibres are simultaneously bonded together. In one preferred embodiment, a viscous solution of a biocompatible polymer is extruded from a spinnaret to form a plurality of filaments which are wound on a rotating mandrel as the spinnaret reciprocates relative to the mandrel. The filaments are wet as they contact each other, so that on evaporation of the solvent the fibres become bonded to each other.

10 Claims, 14 Drawing Figures

IMPLANTABLE MATERIAL

REFERENCE TO RELATED APPLICATION

This application is a continuation-in-part of pending U.S. patent application Ser. No. 309,692 filed Oct. 8, 1981 now abandoned.

FIELD OF INVENTION

The present invention relates to porous material, suitable for in vivo biocompatible implantation and a variety of non-medical applications.

BACKGROUND TO THE INVENTION

It is known from U.S. Pat. No. 3,490,975 to provide an artificial artery or vascular graft by winding extruded silicone rubber thread onto a mandrel so as to form a porous tube. The tube then is cured and the cured tube is removed from the mandrel. The curing step is required to achieve fibre-to-fibre bonding and to form a stabilized structure, in view of the nature of the material used to form the tube. In a typical example of this procedure, thread of 180 to 190 micron thickness is used at a helix angle of 35° to the axis of the mandrel to produce a product having a porosity of 80%. Such fibre size provides side wall openings which are too large to permit proper use of the product as a vascular graft.

SUMMARY OF INVENTION

In accordance with the present invention, there is provided an improved procedure for formation of a porous tubular material, suitable for use, for example, as a vascular graft, by winding extruded material onto a mandrel while simultaneously providing fibre-to-fibre bonding between overlying fibres. This procedure avoids the necessity to postcure the tube to achieve fibre-to-fibre bonding, such as is employed in the prior art procedure discussed above.

The physical characteristics of the product obtained by this novel procedure depend to some extent on the material from which the tubular material is formed. The description which follows relates mainly to the formation of vascular grafts, which requires the utilization of biocompatible and biocompliable material and the formation of a flexible product of high suturing strength and high toughness to resist cyclic fatigue. Anisotropic properties may be obtained by varying the manner of winding of the fibres. It will be understood, however, that products having other physical properties, such as inflexibility, may be formed by the utilization of other materials for the fibre.

When the product of the invention takes the form of a vascular graft, the relatively small pore size therein induces endothelialization of the inner surface of the graft and tissue ingrowth into the outer surface when positioned in the body. The phenomenon of endothelialization of porous vascular graft surfaces is described in Canadian Pat. No. 1,092,303 in the name of David C. MacGregor.

As set forth in that patent, nucleated cells in the bloodstream colonize onto the porous surface and subsequently differentiate into other cell types. The tissue coating organizes over about a one to three month period, does not appear to increase significantly in thickness thereafter and includes flattened endothelial-like cells at the surface thereof.

GENERAL DESCRIPTION OF INVENTION

Vascular grafts may vary in dimensions over wide ranges, depending on the size and type of the blood vessel that they are to replace. The inside diameter may vary widely from about 1 mm to about 50 mm, typically 3 to about 25 mm, and is dictated by the diameter of the mandrel on which the graft is formed. The wall thickness may vary from about 0.1 to about 2 mm, typically about 0.5 to about 1 mm and is controlled by the number of layers of windings formed on the mandrel.

The pore size of the porous structure of the graft may be varied by varying the thickness of the fibres and angle of winding. The pore size is considered the shortest distance between two fibres located in the same plane and usually is, in the longer dimension, about 5 to about 1000 microns, typically about 10 to about 100 microns.

The porosity of the graft is largely dependent on the angle of winding. In addition, compression of the graft prior to drying and removal from the mandrel serves to alter the porosity, so that variation of the porosity over a wide range may be achieved by a combination of these procedures. The porosity may vary from 5 to about 85 vol. %, typically about 50 to about 80 vol. %.

The graft is required to have a minimum strength in use consistent with the requirements that the graft may be sutured readily without tearing and that the graft have sufficient strength to prevent structural breakdown at the anastomosis and along the length of the graft. Such characteristics are provided by the vascular graft of this invention.

The actual minimum strength requirements will vary depending on the intended use of the graft, the strength requirements for venous grafts being very much less than those for arterial grafts because of the lower venous blood pressures. The grafts provided for venous use should be able to withstand venous blood pressure of not less than 25 mm Hg for prolonged periods, generally greater than one year, preferably greater than 5 years, in a physiological environment. An arterial graft should be able to withstand pulsatile arterial blood pressure of greater than about 300 mm Hg, preferably greater than about 500 mm Hg, for a prolonged period of time, generally greater than five years, preferably greater than ten years, in a physiological environment.

The non-woven structure which is formed on the mandrel utilizing the procedure of this invention may be utilized for a variety of bio-medical applications other than as a vascular graft and for a variety of non-medical applications. The tubular structure may be cut to form a flat sheet, or may be otherwise shaped, for utilization in A-V shunts, sewing rings for heart valves, sewing patches for heart wall and blood vessels, artificial blood pump diaphragms, and many other implant and bio-medical applications in dental, orthopaedic and plastic surgery areas, and additionally in many non-medical applications.

DESCRIPTION OF PREFERRED EMBODIMENTS

In one embodiment of the present invention, a biocompatible polymeric material from which the tubular material is to be constructed, for example, a biocompatible polyurethane, is dissolved in a suitable solvent to form a viscous solution from which a continuous fibre may be drawn.

The solution is extruded under pressure through an opening and a continuous filament of desired thickness is drawn from the extruded material, typically less than about 100 microns, preferably to a filament thickness of about 0 to about 30 microns. The opening through which the solution is extruded may typically be about 4 to 5 times the diameter of the filament drawn from the extruded material.

In order to increase the speed of formation of the tubular material, it is preferred to wind a plurality of filaments on the mandrel simultaneously, by housing the polymer solution in a spinnaret having a plurality of extrusion openings and drawing a fibre from each extrusion opening.

The drawn fibre is placed in contact with a rotating mandrel. The diameter of the mandrel determines the inside diameter of the tube which is formed. The spinnaret from which the filaments are extruded then reciprocates from one axial end of the fixed position mandrel to the other and parallel thereto at a speed which results in the filaments subtending any desired angle to the mandrel, so that the filaments laid in one traverse of the mandrel in one direction and the filaments laid in the previous traverse of the mandrel in the opposite direction criss-cross each other, to form a porous structure.

The angle of winding of the fibres with respect to the axis of the mandrel may vary widely, generally from about 10° to 80°, preferably about 45° to 80°. As the angle of winding is decreased, the pore size and the porosity of the graft also decrease, while the shape of the pores also changes.

The reciprocation of the spinnaret with respect to the mandrel is continued until the desired thickness of overlayed filaments is obtained. Usually the mandrel is mounted extending horizontally while the spinnaret is vertically spaced from the mandrel to reciprocate along an axis parallel to the axis of the mandrel.

The solution form of the polymer at the time of formation of the filaments means that the filaments are "wet" when they are laid on the mandrel and this results in firm secure bonding of the filaments to each other through integral joining at their overlapping points upon evaporation of the solvent, to form a stable non-woven structure without any further processing. Evaporation of the solvent may be enhanced by the application of heat during the winding of the filaments on the mandrel, and subsequent to completion of the winding operation, if required. Exposing the tube to infra-red radiation has been found to be a suitable manner of achieving the application of heat.

When the desired thickness of tubular product has been achieved, the porous structure is washed free from residual solvent and removed from the mandrel. As mentioned above, the tubular product may be compressed prior to removal from the mandrel to alter the porosity and pore size. The washed product then is dried.

The thickness of the individual fibres in the non-woven structure which results from the above-described procedure may be controlled by the ratio of the flow rate of polymer solution and the speed of rotation of the mandrel. The size and shape of the openings or pores defined by the fibres in the non-woven structure may be controlled by the angle subtended by the fibres to the mandrel and the fibre diameter.

The procedure just described is suitable for use with polymeric materials which form viscous solutions in volatile solvents from which continuous fibres may be drawn. The procedure of the invention may be used in modified form with other polymeric materials, such as, polyethylene.

In such a modified procedure, extruded fibres are provided in a tacky fusible substantially solvent-free form in the overlaid condition following winding of the fibres on a mandrel so that fibre-to-fibre bonding occurs and the non-woven structure is provided as the fibres solidify. The tacky fusible form of the fibres may be provided in any convenient manner, such as, by hot extruding the fibres from a melt of the polymer and forming the overlying layers while the fibres are still hot and fusible. Alternatively, the mandrel may be heated to provide the heat required for fusion of the overlayed fibres as they are wound on the mandrel. The latter procedure may be enhanced by using fibres which are still hot from the extrusion.

The procedure of the invention, therefore, enables non-woven porous tubular products to be formed directly from extruded filaments without the necessity of post-treatment to form an integrated strcture. The porous tubular products may be used as such, for example, as vascular grafts, may be used in modified form in various bio-medical applications, or may be used as such or in modified form in non-medical applications.

Figure 1:
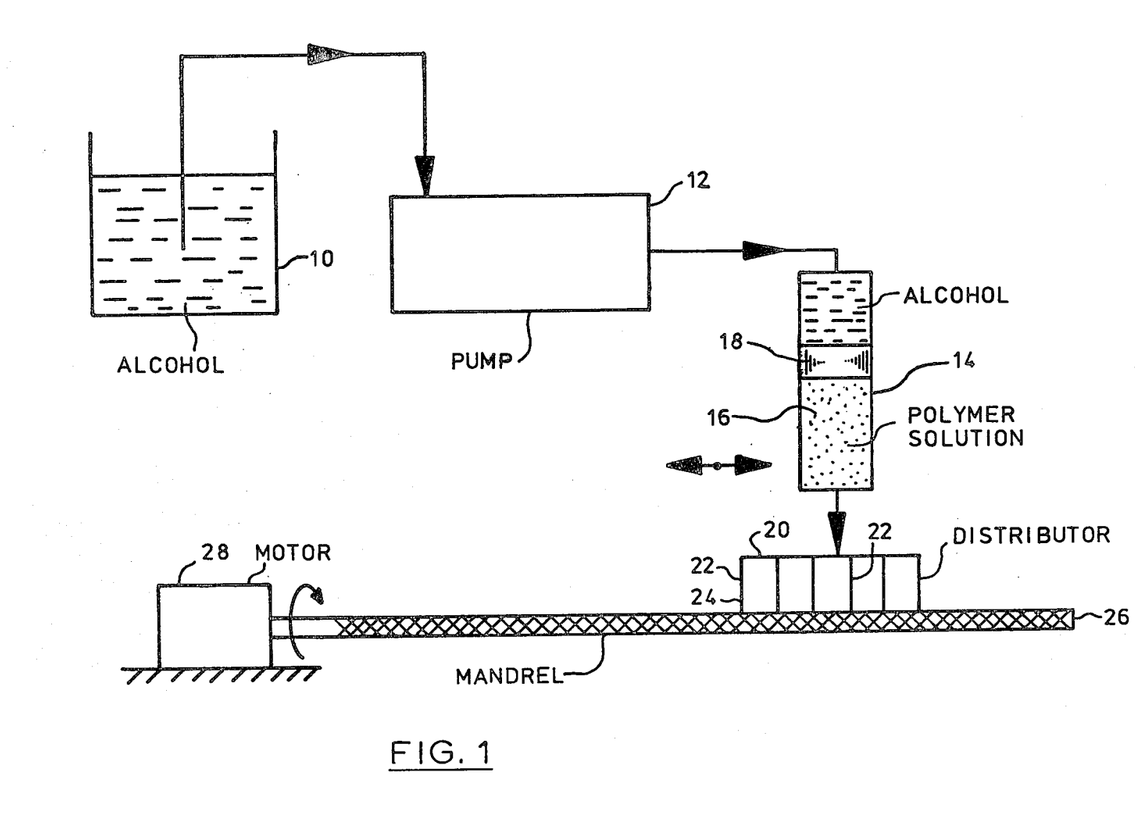
FIG. 1 is a schematic representation of an apparatus used to effect the present invention.

Referring to FIG. 1, alcohol is pumped from a tank 10 by a volumetric pump 12 into a high pressure cylinder 14 containing a polymer solution 16 which is separated from the alcohol by a plunger 18. This arrangement is used to avoid pumping high viscosity polymer solution through a precision pump.

The plunger 18 is pushed by the alcohol and the plunger 18, in turn, pushes the polymer solution through a distributor 20 into six orifices 22. The polymer solution is extruded through the orifices to form fibres 24 which are wound onto a rotating mandrel 26. The mandrel 26 is rotated by motor 28. A high circumferential speed of the mandrel 26 results in stretching of the fibres 24.

The distributor 20 reciprocates along the length of the mandrel 26 until the desired thickness of tube has been formed. For example, approximately 800 to-and-fro passes of the distributor 20 are needed to produce a 6 mm I.D. tube having 500 micron thick walls.

The effect of variation of winding angle on the physical properties of the resulting product were determined. The results are reproduced in the following Table I:

TABLE I

| Winding Angle | Fibre[1] Dia. (μm) | Porosity % | Pore Size[2] (μm) | Stiffness[3] N/mm (10% Elong.) | Min. kinking[4] Dia. (cm) | Wall Thickness (mm) | Number of Passes |
|---|---|---|---|---|---|---|---|
| 45° | 16.4 | 75 | 35.7 | 5.17 | 3.8 | 0.55 | 1000 |
| 45° | 30.0 | 87 | 146.8 | 4.72 | 2.3 | 0.59 | 180 |
| 60° | 16.4 | 74 | 33.5 | 1.51 | 1.3 | 0.51 | 720 |
| 80° | 16.4 | 67 | 22.4 | 0.49 | 0.3 | 0.65 | 322 |

Notes:
[1]Calculated from the expression:

$$d_f = \sqrt{\frac{4000 \dot{V} S}{\pi n \sqrt{(V_1^2 + V_2^2)}}}$$

where $\dot{V}$ is the pumping rate in cc/min, S is the volume fraction of polymer in solution, $d_f$ is the fibre diameter in mm, n is the number of extrusion nozzles and $V_1$ and $V_2$ are respectively the circumferential velocity of the mandrel and the longitudinal velocity of the carriage in mm/min.
[2]Calculated from porosity and fibre diameter.
[3]Force required to elongate a 6 mm I.D. graft having a 1 mm thick wall.
[4]Minimum diameter of rod about which the tube can bend without collapsing.

EXAMPLES

Example 1

A woven vascular graft was prepared using the apparatus which is schematically depicted in FIG. 1. A 45% w/w solution of a hydrophilic segmented polyether-polyurethane urea block copolymer in dimethyl formamide was extruded from a housing having six orifices at a flow rate of 0.1 cc/min. Six fibres were simultaneously wound on the mandrel which rotated at a speed of 900 rpm and had a diameter of 10 mm while the housing was reciprocally driven relative to the mandrel to provide an angle of winding of 45°. A sufficient number of passes were made to provide a wall thickness of tube of about 850 microns. During the formation of the graft, solvent evaporation and fibre drying were assisted by the utilization of an I.R. lamp.

The drawn fibres were not completely dry as they were laid on each other and bonded together on contact with each other to form a non-woven fabric tube. Once the tube had dried under the I.R. lamp, it was soaked in water to remove residual solvent and then slid from the rod. The tube exhibited elasticity and flexibility.

Figure 2:
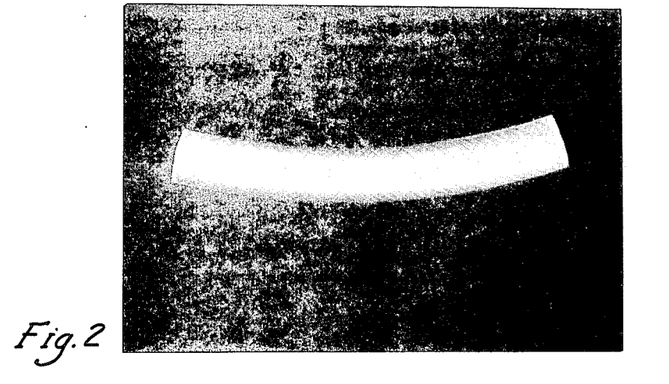
FIG. 2 is a photograph of a medium caliber vascular graft provided in accordance with one embodiment of the invention.
Figure 3:
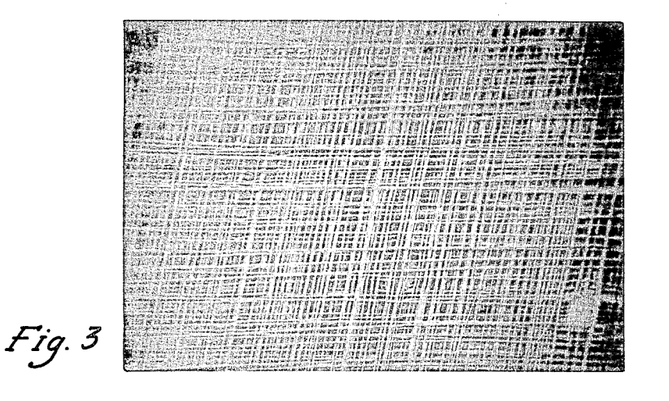
FIG. 3 is scanning electron micrograph of the surface of the graft of FIG. 1 at 20× magnification.
Figure 4:
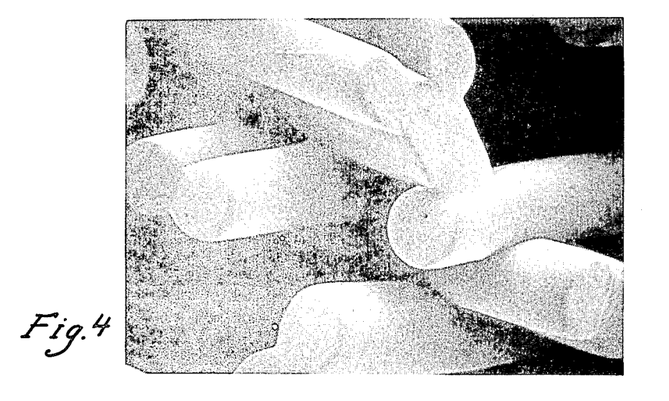
FIG. 4 is a scanning electron micrograph of an edge of the vascular graft of FIG. 2 at 1000 times magnification.
Figure 5:
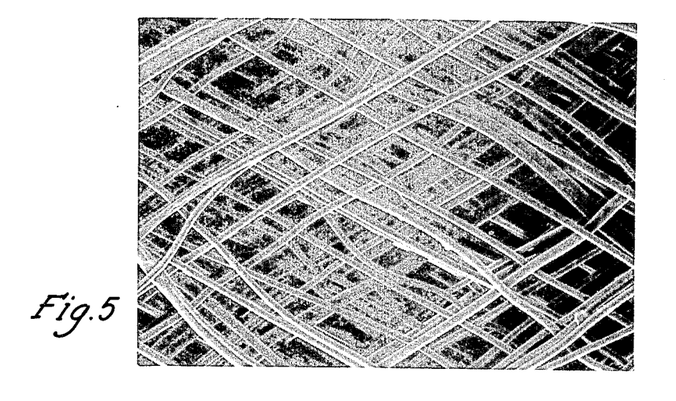
FIGS. 5 to 8 are scanning electron micrographs at 150× magnification of the inside surface of four vascular grafts consisting of fibres of nominal diameters 13, 16, 20 and 30 microns respectively.
Figure 6:
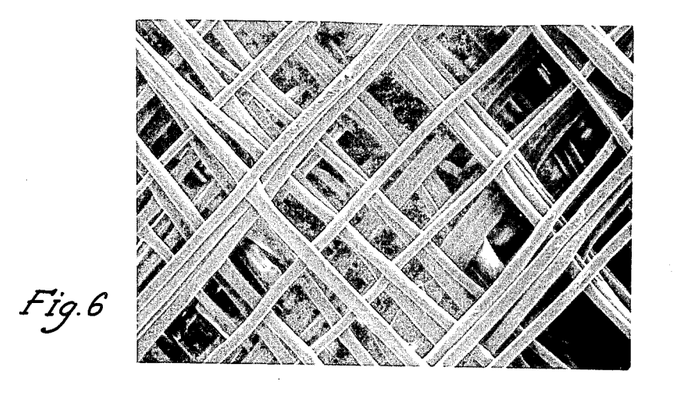
Figure 7:
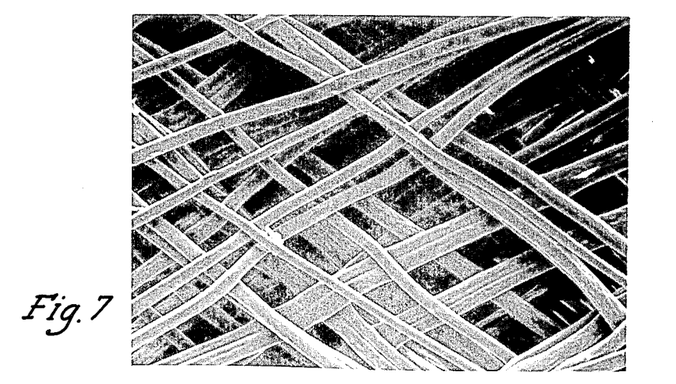
Figure 8:
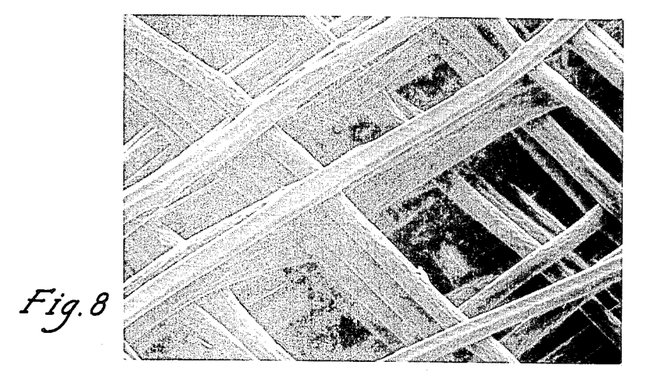

The structure of the graft which was formed is shown in the accompanying FIGS. 2 to 4. FIG. 2 is a a photograph of the overall appearance of the graft while FIG. 3 is an SEM of the outer surface of the graft at 20× magnification and FIG. 4 is an SEM of an edge of the graft at 1000× magnification, clearly showing the fused nature of the overlying fibres.

Example 2

The procedure of Example 1 was repeated using a 40% solution of a polyurethane (Pellethane 2363-75DX) dissolved in dimethyl formamide to form nonwoven material tubes. Grafts were produced from fibres of varying diameters of 13, 16, 20 and 30 microns. Scanning electron micrographs of the inside surface of the grafts appear as FIGS. 5 to 8 respectively.

As may be seen from the results of Table I, the porosity and pore size of the product decline as the winding angle is increased. Further, the stiffness and minimum kinking diameter declined significantly as the winding angle increased. These variations enable a balance of the properties of pore size, porosity, stiffness and minimum kinking diameter to be achieved by varying the winding angle.

Figure 9:
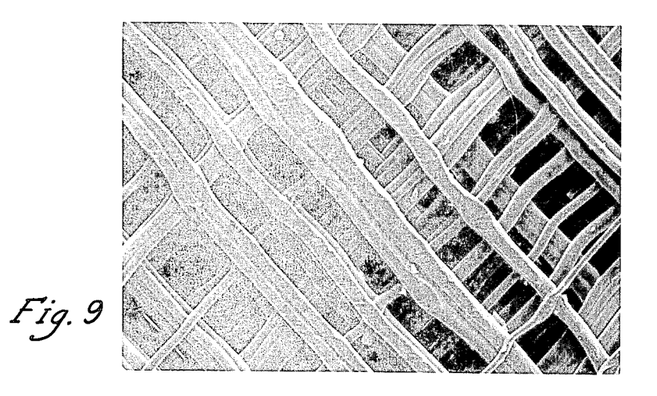
FIGS. 9 and 10 are scanning electron micrographs at 150 times magnification of the inside surface of two vascular grafts formed at winding angles of 30° and 80° respectively.
Figure 10:
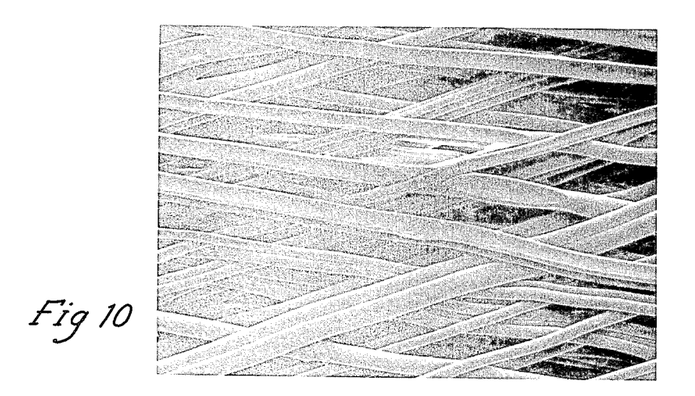

The physical appearance of grafts produced at angles of winding of 30° and 80° appears in FIGS. 9 and 10 respectively. As may be seen therein, altering the angle of winding from 30° to 80° decreases the porosity by over 10% and the pore size from about 45 to about 21 microns.

Example 3

Two prototype vascular grafts produced by the procedure of Example 2 were tested in vivo. One graft was a medium caliber graft having an internal diameter of 10 mm and a wall thickness of 858 microns while the other graft was a small caliber graft of internal diameter of 4 mm and a wall thickness of 822 microns.

5 cm length of the medium and small caliber grafts were interposed between segments of the abdominal aorta and left carotid artery of two dogs, respectively. Both dogs were sacrified three months after implantation and the grafts examined grossly and by light and scanning electron microscopy.

Figure 11:
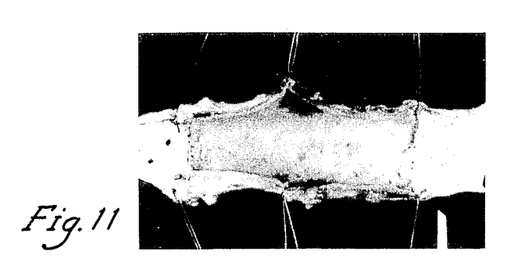
FIGS. 11 to 14 are micrographs of the graft of FIG. 2 after being interposed in the abdominal aorta of a dog for three months, with FIG. 11 being a light micrograph of the gross appearance of the graft showing the unfiorm, smooth, glistening neo-intima with a complete absence of gross thrombi, FIG. 12 being a scanning electron micrograph at 70× magnification of the distal anastomosis, FIG. 13 being a scanning electron micrograph at 500× magnification of the mid-portion, and FIG. 14 being a light micrograph at 40× magnification of a cross-section of the graft showing the neointima on the inner surface, transmural growth of fibrovascular tissue and outer tissue encapsulation.

The medium caliber aortic graft was found to be widely patent and lined by a uniform, smooth, glistening neo-intima completely devoid of gross thrombi. Light microscopy of the graft (FIG. 11) showed the uniform, smooth, glistening neo-intima with a complete absence of gross emboli.

Figure 12:
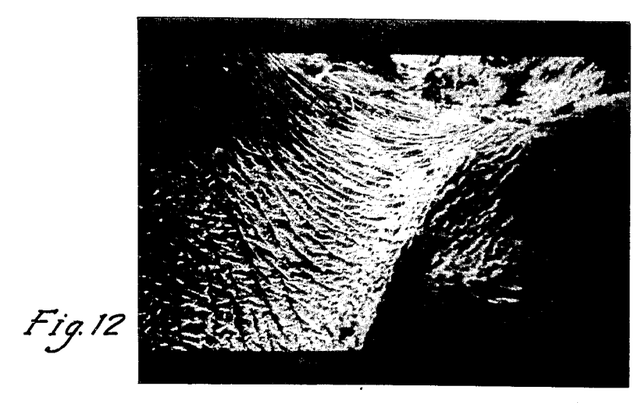
Figure 13:
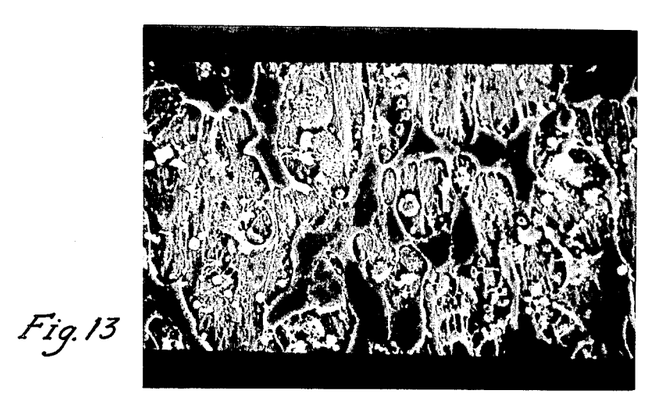
Figure 14:
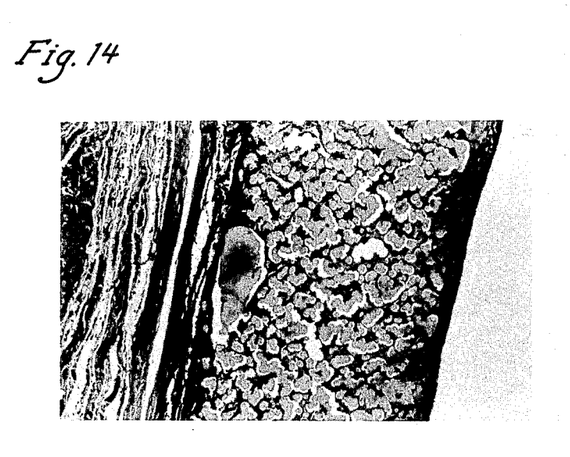

Scanning electron microscopy showed complete endothelialization of the anastomotic sites (FIG. 12) and patchy endothelialization of the mid-portion of the graft with the intervening areas being covered by branching collagen bundles to which platelets and strands of fibrin were adhering (FIG. 13). Light microscopy of a cross-section of the graft (FIG. 14) confirmed the presence of a neo-intimal lining with transmural growth of fibrovascular tissue and outer tissue encapsulation.

The small caliber carotid graft was also widely patent with a similar uniform, smooth, glistening neo-intima. The appearance of the neo-intima on scanning electron and light microscopy was similar to that formed on the medium caliber graft.

SUMMARY OF DISCLOSURE

In summary of this disclosure, porous tubular products, suitable for use in implantable bio-medical devices and having other non-medical uses, are formed by a unique procedure. Modifications are possible within the scope of this invention.

The embodiments of the invention in which an exclusive property or privilege is claimed are defined as follows:

1. A method of forming a porous flexible biocompatible and biocompliable tubular vascular graft, which comprises:
   extruding an extrudable biocompatible and biocompliable thermoplastic polymeric material through an opening having a diameter larger than the intended diameter of fibers to be drawn therefrom, said polymeric material being capable of forming flexible fibres therefrom,
   drawing a continuous fibre of diameter of less than about 100 microns from said extruded material by attenuating the extruded material using a drawing force applied longitudinally of the fibre,
   winding said continuous fibre on a mandrel having a diameter of about 1 to about 50 mm while simultaneously providing fibre-to-fibre bonding between overlying fibres as the continuous fibre subtends an angle of about 10° to about 80° to the axis of the mandrel until a thickness of about 0.1 to about 2 mm has been formed on said mandrel to form a porous tubular product having a porosity of about 50 to about 80 volume percent on said mandrel,
   rotating said mandrel on its axis at sufficient speed during said winding to apply said longitudinal drawing force to said fibre to effect the drawing and attenuation of said continuous fibre from said extruded polymeric material, and
   removing said porous tubular product from said mandrel to provide said porous flexible biocompatible and biocompliable tubular vascular graft.

2. The method of claim 1 wherein said extrudable polymeric material takes the form of a viscous solution of a polymeric material from which a fibre may be drawn, and wherein said fibre-to-fibre bonding is achieved by removal of said solvent from said overlying fibres.

3. The method of claim 2 wherein said mandrel is heated to assist in evaporation of solvent from said overlying fibres to achieve said fibre-to-fibre bonding.

4. The method of claim 1 wherein said extrudable polymeric material takes the form of a molten polymeric thermoplastic material and wherein said fibre-to-fibre bonding is achieved by fusion of overlying fibres and solidification of the fused fibres.

5. The method of claim 1 including the further step of cutting said porous tubular product after said removal from said mandrel to form a planar sheet of porous material.

6. A method of forming a porous flexible biocompatible and biocompliable tubular vascular graft, which comprises:
   extruding an extrudable biocompatible and biocompliable thermoplastic polymeric material through a plurality of openings in a spinnaret containing said polymeric material, each of said openings having substantially the same diameter and larger than the intended diameter of fibres to be drawn therefrom, said polymeric material being capable of forming flexible fibres therefrom,
   drawing a plurality of individual continuous fibres of diameter of about 10 to about 30 microns from the extruded polymeric material by attenuating the extruded material using a drawing force applied longitudinally of the fibre,
   winding said plurality of fibres onto a mandrel having a diameter of about 1 to about 50 mm by rotating said mandrel on its axis while simultaneously providing fibre-to-fibre bonding between overlying fibres,
   reciprocating said spinnaret relative to said mandrel as said mandrel rotates on its axis and the continuous fibres subtend an angle of about 10° to about 80° to the axis of the mandrel until a thickness of about 0.1 to about 2 mm has been formed on said mandrel to form a porous tubular product having a porosity of about 50 to about 80 volume percent and pore openings of about 10 to about 100 microns on said mandrel,
   rotating said mandrel on its axis at sufficient speed during said winding to apply said longitudinal drawing force to each of said continuous fibres to effect said drawing of said fibres from said extruded polymeric material and attenuation of said fibres, and
   removing said porous tubular product from said mandrel to provide said porous flexible biocompatible and biocompliable tubular vascular graft.

7. The method of claim 6 wherein said rotating mandrel is located with its axis substantially horizontal and said spinnaret reciprocates parallel to said mandrel axis.

8. The method of claim 6 wherein said fibres are extruded through openings in said spinnaret which are about 4 to 5 times larger than the diameter of the drawn fibres.

9. The method of claim 6 wherein said angle is about 60° to 70°.

10. The method of claim 6 wherein said mandrel diameter is about 3 to about 25 mm and said thickness is about 0.5 to about 1 mm.